United States Patent [19]

Mahler et al.

[11] Patent Number: 5,723,429
[45] Date of Patent: Mar. 3, 1998

[54] AZEOTROPIC OR AZEOTROPE-LIKE COMPOSITIONS OF TETRAFLUOROETHANE AND CHLOROTETRAFLUOROETHANE

[75] Inventors: Barry Asher Mahler, Glen Mills, Pa.; Ralph Newton Miller, Newark; Charles Joseph Noelke, Wilmington, both of Del.

[73] Assignee: E. I. du Pont de Nemours and Company, Wilmington, Del.

[21] Appl. No.: 637,119

[22] Filed: Apr. 24, 1996

Related U.S. Application Data

[60] Division of Ser. No. 471,937, Jun. 6, 1995, abandoned, which is a continuation-in-part of Ser. No. 212,439, Mar. 11, 1994, Pat. No. 5,470,442.

[51] Int. Cl.$^6$ ............................... C11D 7/30; C09K 5/04
[52] U.S. Cl. ........................... 510/408; 252/67; 510/177
[58] Field of Search ................................. 252/67; 510/177, 510/408; 203/63, 65, 64, 56, 51, 66, 71, 67; 570/178, 170, 177

[56] References Cited

U.S. PATENT DOCUMENTS

| | | | |
|---|---|---|---|
| 3,607,755 | 9/1971 | Murphy et al. | 252/67 |
| 3,732,150 | 5/1973 | Bailey | 203/50 |
| 3,819,493 | 6/1974 | Fozzard | 203/70 |
| 4,810,403 | 3/1989 | Bivens et al. | 252/67 |
| 4,906,796 | 3/1990 | Yates | 570/179 |
| 4,996,379 | 2/1991 | Oshio et al. | 570/176 |
| 5,035,823 | 7/1991 | Tamura et al. | 252/67 |
| 5,200,431 | 4/1993 | Dattani et al. | 203/64 |
| 5,211,020 | 5/1993 | Taylor et al. | 62/11 |
| 5,243,105 | 9/1993 | Scott et al. | 570/169 |
| 5,306,850 | 4/1994 | Darago | 570/178 |
| 5,334,786 | 8/1994 | Koyama et al. | 570/168 |
| 5,336,377 | 8/1994 | Yates et al. | 203/29 |
| 5,425,890 | 6/1995 | Yudin et al. | 252/67 |
| 5,461,177 | 10/1995 | Manzer et al. | 570/178 |
| 5,463,152 | 10/1995 | Rao | 570/176 |
| 5,470,442 | 11/1995 | Mahler et al. | 203/56 |
| 5,475,168 | 12/1995 | Masiero et al. | 570/177 |
| 5,523,011 | 6/1996 | Jones | 252/67 |
| 5,622,644 | 4/1997 | Stevenson et al. | 252/67 |
| 5,632,928 | 5/1997 | Jackson | 252/67 |
| 5,635,099 | 6/1997 | Bivens et al. | 252/67 |
| 5,648,017 | 7/1997 | Bartlett et al. | 252/67 |

FOREIGN PATENT DOCUMENTS

| | | |
|---|---|---|
| 467531 | 1/1992 | European Pat. Off. . |
| 0 472 391 | 2/1992 | European Pat. Off. . |
| 574 756 | 12/1993 | European Pat. Off. . |
| 583 551 | 2/1994 | European Pat. Off. . |
| 0 626 362 | 11/1994 | European Pat. Off. . |
| 4-316 525 | 11/1992 | Japan . |
| 4-321 632 | 11/1992 | Japan . |
| 471 760 | 6/1969 | Switzerland . |
| 1 578 933 | 11/1980 | United Kingdom . |

OTHER PUBLICATIONS

D. G. Ghering et al., Journal Of Chromatographic Science, 30, 280–284, 1992 (Jul.).

Harold R. Null, Phase Equilibrium in Process Design, *Wiley Interscience*, 124–126, 1970.

Reid, Prausnitz & Poling, The Properties Of Gases & Liquids, 4th Edition, *McGraw Hill*, 241–387, (no date provided).

Stanley M. Walas, Phase Equilibrium In Chem. Eng., *Butterworth Publishers*, 165–244, 1985.

*Primary Examiner*—Douglas J. McGinty
*Attorney, Agent, or Firm*—James E. Shipley

[57] ABSTRACT

The disclosure relates to separating 1,1,2,2 tetrafluoroethane (HFC-134) and 1,1,1,2 tetrafluoroethane (HFC-134a) from each other and/or from fluorocarbon impurities by using extractive distillation with an extractive agent comprising an alcohol. Examples of suitable extractive agents comprise at least one member from the group of methanol, butanol, ethanol, propanol, their isomers and cyclic compounds thereof, among others.

1 Claim, 7 Drawing Sheets

AZEOTROPIC OR AZEOTROPE-LIKE COMPOSITIONS OF TETRAFLUOROETHANE AND CHLOROTETRAFLUOROETHANE

CROSS-REFERENCE TO RELATED APPLICATION

This is a division of application Ser. No. 08/471,937 filed Jun. 6, 1995, now abandoned, which is continuation-in-part of application Ser. No. 08/212,439, filed Mar. 11, 1994, now U.S. Pat. No. 5,470,442, in the names of Barry Asher Mahler and Ralph Newton Miller, and entitled "Separating And Removing Impurities From Tetrafluoroethanes By Using Extractive Distillation", the disclosure of which is hereby incorporated by reference.

FIELD OF THE INVENTION

The instant invention relates to the field of removing impurities from tetrafluoroethanes by using an extractive distillation process that employs alcohols.

BACKGROUND OF THE INVENTION

Conventional methods for manufacturing 1,1,1,2 tetrafluoroethane, or its isomer 1,1,2,2 tetrafluoroethane typically contain undesired impurities.

There is a need for a method to obtain high purity non-chlorine-containing fluorocarbons such as 1,1,1,2 tetrafluoroethane ($CF_3CH_2F$), also known as hydrofluorocarbon 134a (HFC-134a), and its isomer, 1,1,2,2 tetrafluoroethane ($CF_2HCF_2H$ or HFC-134). These fluorocarbons are useful as refrigerants, blowing agents, cleaning agents, aerosol propellants, heat transfer media, fire extinguishing agents, power cycle working fluids, polymerization media, particulate removal fluids, carrier fluids, buffing abrasive agents, displacement drying agents, among many other applications.

SUMMARY OF THE INVENTION

Hydrogenolysis can be employed for manufacturing tetrafluoroethane products, i.e., HFC-134a and HFC-134. For example, a process for manufacturing HFC-134a and HFC-134 by hydrodehalogenating CFC-114 and/or CFC-114a is disclosed in Great Britain Patent No. 1,578,933, U.S. Pat. No. 4,996,379, and Journal of Chromagraphic Science, Vol. 30, Pages 280 through 284 (1992) by D. G. Ghering et al.; the disclosure of which is hereby incorporated by reference. Because of varying isomer purities in the starting material, or due to isomerization during the hydrodehalogenation, the product mixture typically contains both 134a and 134 isomers. Due to the nature of the chemistry, the product may also contain a variety of other non-tetrafluoroethane isomer co-products, such as chlorotetrafluoro-ethanes, dichlorotetrafluoroethanes, trifluoroethanes, difluoroethanes, a variety of single carbon halogenated products, two carbon unsaturated halogenated products, among other impurities. The presence of even relatively small amounts of the other isomer or impurities in either tetrafluoroethane product is undesirable in many applications of these products, e.g., more than about 50 ppm of compounds such as HCFC-31 and HCFC-1112 can be harmful. Chlorofluorocarbon impurities such as CFC-12 are considered environmentally harmful and are being regulated out of the marketplace. While certain impurities in the tetrafluoroethane product can be readily removed by conventional distillation, small amounts of certain other close-boiling impurities are difficult, if not impossible, to remove by using conventional methods.

In particular HFC-134 and HFC-134a are very difficult to separate from each other by using conventional distillation because of their close atmospheric boiling points: −26.5 degrees C. for HFC-134a and −19.7 degrees C. for HFC-134. The relative volatility of HFC-134a to HFC-134, when approaching 100% pure HFC-134a, is about 1.20 at 0 degrees C., which makes for an extremely difficult separation that requires large and expensive distillation columns.

There is a need for an extractive distillation procedure which will separate HFC-134a from HFC-134 and remove other close-boiling fluorocarbon impurities from HFC-134a and/or HFC-134.

We have found that 1,1,2,2 tetrafluoroethane (HFC-134) can be separated from 1,1,1,2 tetrafluoroethane (HFC-134a) by using extractive distillation with an extractive agent comprising or consisting essentially of an alcohol such as at least one of methanol, butanol, ethanol, propanol, isomers and cyclic compounds thereof, among others. While other compounds containing a hydroxyl (—OH) group can be used as an extractive agent, such compounds are less desirable than the aforementioned alcohols. Such hydroxyl containing compounds would necessitate usage of relatively expensive apparatus and process conditions, e.g., thereby increasing energy costs.

We have also found that other fluorocarbon impurities such as at least one of chlorofluoromethane (HCFC-31), chlorodifluoromethane (HCFC-22), 2-chloro-1,1-difluoroethylene (HCFC-1122), 1-chloro-1,1,2,2-tetrafluoroethane (HCFC-124a), chloropentafluoroethane (CFC-115), dichlorodifluoromethane (CFC-12), 1,1-difluoroethane (HFC-152a), among many other compounds, can be removed from the tetrafluoroethanes concomitantly and/or in a separate operation by using the inventive process.

It was surprising and unexpected that the inventive process can separate two isomers of the same chemical compound, i.e., which by definition have an identical chemical composition and differ only in atomic arrangement, because an effective extractive distillation agent must in some way interact differently with the two compounds. It was heretofore unknown that an alcohol or a hydroxyl containing extractive agent would interact differently with two chemical isomers such that these two isomers can be separated by using extractive distillation. It was also surprising and unexpected that the alcohol containing extractive agent can permit the simultaneous removal other fluorocarbon impurities from the isomers.

DETAILED DESCRIPTION

Figure 1:
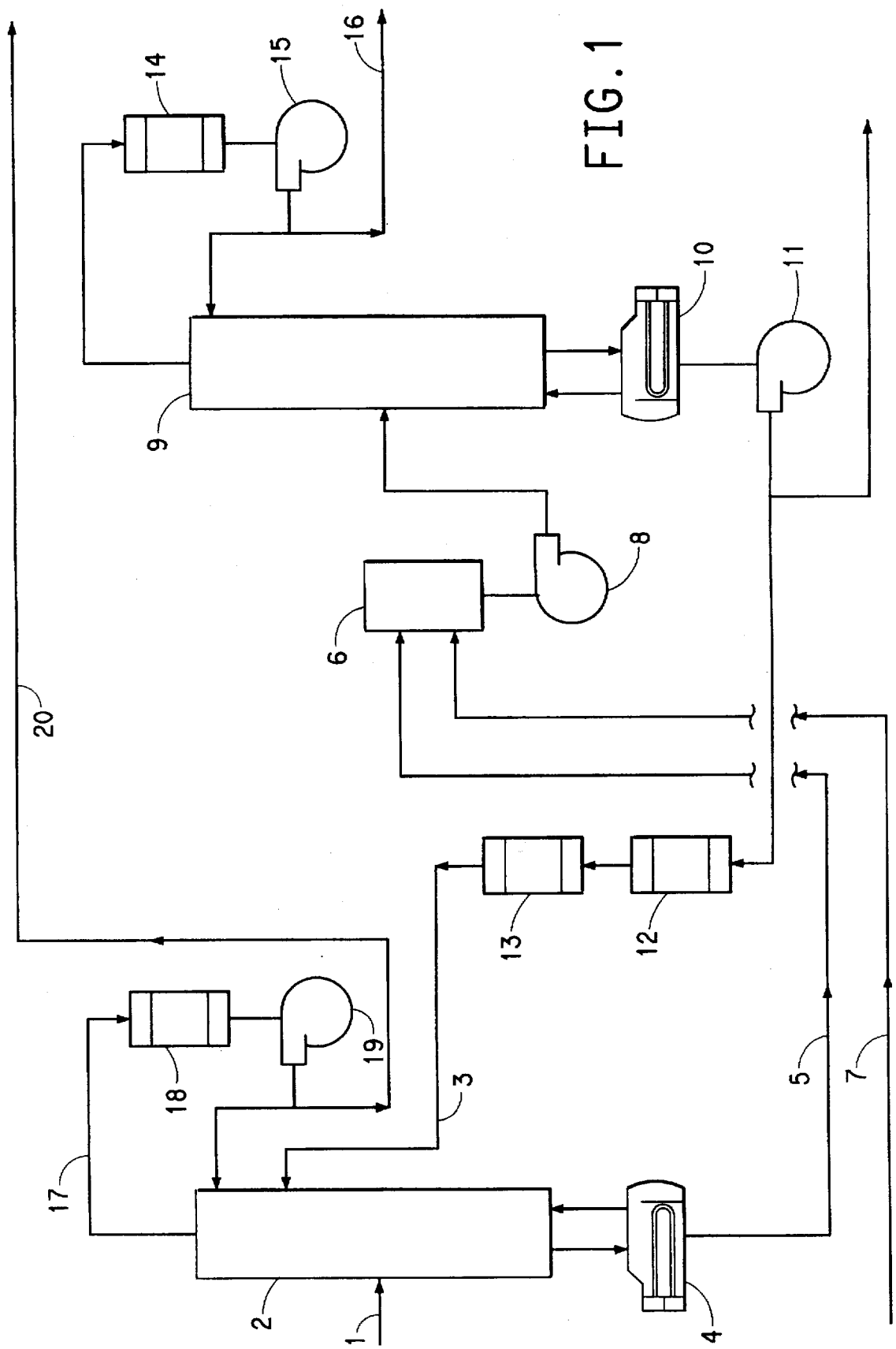
FIG. 1—FIG. 1 is a schematic diagram of an extractive distillation system that can be used for practicing an aspect of the inventive process.

HFC-134a and HFC-134, which are the primary constituents of a first mixture, in their separated and pure states have boiling points, respectively, of about −26.5° and about −19.7° C. The relative volatility at around 0° C. was found to be about 1.2 as 100% 134a and about 1.3 as 100% 134 was approached. These data indicate that it would be extremely difficult to use conventional distillation procedures for separating the two tetrafluoroethane isomers to obtain a tetrafluoroethane isomer which is substantially free of the other isomer. By "substantially free", it is meant that the desired tetrafluoroethane isomer product contains less than about 1.0 wt % of the undesired isomer or other impurity, normally less than about 0.05 wt %, and in some cases less than about 10 ppm by weight.

To determine the relative volatility of HFC-134 and HFC-134a the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126; the entire disclosure of which is hereby incorporated by reference.

These measurements can be converted into equilibrium vapor and liquid compositions in the PTx cell by using an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids, 4th edition, publisher McGraw Hill, written by Reid, Prausnitz and Poling, on pages 241 to 387; and in "Phase Equilibria in Chemical Engineering, published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not HFC-134 and HFC-134a mixtures and/or the following other mixtures behave in an ideal manner, and can sufficiently predict the relative volatilities of the components in such mixtures.

The results of PTx measurements and the above series of calculations are summarized below in Tables 1 through 3, giving relative volatility for the HFC-134a/HFC-134 system, the HFC-134a/methanol system and the HFC-134/methanol system.

TABLE 1

Vapor-Liquid Measurements on the HFC-134a/HFC-134 System at 0.1 deg. C.

| Mole Fraction, HFC-134 | | Pressure | Relative Volatility |
|---|---|---|---|
| in Liquid | in Vapor | (psia) | HFC-134a/HFC-134 |
| 0.00 | 0.00 | 42.63 | 1.20 |
| 0.17 | 0.14 | 41.56 | 1.23 |
| 0.29 | 0.24 | 40.25 | 1.24 |
| 0.34 | 0.29 | 40.07 | 1.25 |
| 0.44 | 0.38 | 39.00 | 1.26 |
| 0.50 | 0.44 | 38.36 | 1.27 |
| 0.63 | 0.57 | 36.91 | 1.29 |
| 0.78 | 0.73 | 35.27 | 1.31 |
| 0.92 | 0.89 | 33.95 | 1.32 |
| 1.00 | 1.00 | 32.89 | 1.33 |

The "Mole Fraction" column refers to the quantity of HFC-134 that is in the liquid and vapor portions of the HFC-134a/HFC-134 mixture within the PTx Cell.

TABLE 2

Vapor-Liquid Measurements on HFC-134a/Methanol System at 11.2 deg. C.

| Mole Fraction, HFC-134a | | Pressure, | Relative Volatility |
|---|---|---|---|
| in Liquid | in Vapor | (psia) | HFC-134a/Methanol |
| 0.00 | 0.00 | 1.13 | 216.2 |
| 0.13 | 0.96 | 26.75 | 160.6 |
| 0.33 | 0.98 | 48.43 | 97.9 |
| 0.60 | 0.98 | 57.68 | 44.0 |
| 0.80 | 0.98 | 60.08 | 17.2 |
| 0.94 | 0.98 | 61.74 | 5.7 |
| 1.00 | 1.00 | 62.65 | 2.9 |

The "Mole Fraction" column refers to the quantity of HFC-134a that is in the liquid and vapor portions of the HFC-134a/methanol mixture within the PTx Cell.

TABLE 3

Vapor-Liquid Measurements on HFC-134/Methanol System at 11.2 deg. C.

| Mole Fraction, HFC-134 | | Pressure, | Relative Volatility |
|---|---|---|---|
| in Liquid | in Vapor | (psia) | HFC-134/Methanol |
| 0.00 | 0.00 | 1.13 | 102.2 |
| 0.10 | 0.92 | 12.33 | 96.4 |
| 0.26 | 0.97 | 28.54 | 83.0 |
| 0.42 | 0.98 | 39.28 | 64.6 |
| 0.60 | 0.98 | 43.74 | 40.6 |
| 0.85 | 0.99 | 46.08 | 11.9 |
| 0.93 | 0.99 | 47.28 | 6.0 |
| 1.00 | 1.00 | 48.85 | 3.1 |

The "Mole Fraction" column refers to the quantity of HFC-134 that is in the liquid and vapor portions of the HFC-134/methanol mixture within the PTx Cell.

In Tables 1, 2 and 3 above, the "Relative Volatility" were those calculated by using the PTx cell pressure which was measured at the temperature indicated on the above Tables.

While the relative volatility of HFC-134a in comparison to HFC-134 at relatively low concentrations is sufficient to permit separating HFC-134a by using conventional distillation methods, the relative volatility approaches 1.0 as 100% purity of HFC-134a is approached. A relative volatility approaching 1.0 would render removing trace concentrations of HFC-134 from HFC-134a, and visa versa, by using conventional distillation difficult, e.g., conventional distillation would require using large and expensive distillation columns.

Tables 2 and 3 show that methanol can be readily separated from HFC-134a and HFC-134. More importantly, Tables 2 and 3 show that as the amount of methanol in the HFC-134a or HFC-134 increases, or the mole fraction of HFC-134a or HFC-134 approaches zero, the relative volatility of HFC-134a versus methanol and the relative volatility of HFC-134 versus methanol begins to differ dramatically. Comparing Table 2 versus Table 3, at a liquid mole fraction of about 0.94 of HFC-134a and 0.93 of HFC-134, the relative volatilities of HFC-134a and HFC-134 versus methanol are essentially the same: 5.7 or 6.0. However, as a liquid mole fraction of about 0.00 HFC-134a or HFC-134 is approached, the relative volatility of the HFC-134a versus methanol is approximately twice that of HFC-134 versus methanol. This is a surprising and an unexpected result which indicates that adding an extractive agent such as methanol to a mixture comprising HFC-134a and HFC-134 will permit using an extractive distillation process to separate these compounds. Similar PTx measurements were performed by using mixtures of HFC-134a and ethanol or propanol, and HFC-134 and ethanol or propanol. These PTx measurements were employed to develop the extractive distillation examples which are described below in greater detail.

By employing the inventive alcohol containing extractive agent, the problems associated with conventional distillation methods can be solved. "Conventional distillation" is intended to refer to a process wherein the relative volatility only of the components in the mixture to be separated is being used for separation, whereas "extractive distillation" depends upon the ability of certain extractive agents to amplify or increase the relative volatility of the compounds to be separated. Extractive distillation is typically performed by operating a continuous distillation column, which comprises a multi-stage distillation column, with a minimum of two feed points, e.g. introducing the extractive agent at a first feed point which is located above the second feed point that is used for introducing the mixture to be separated, a reboiler, an overhead condenser for returning reflux to the column, among other commercially available apparatus.

Given the close relative volatilities of HFC-134a and HFC-134, it was a surprising and an unexpected result that they can be purified by extractive distillation using certain readily available and low cost fluorine-free compounds. It was also surprising that this same procedure and equipment can simultaneously or separately be used for removing other fluorocarbon impurities from HFC-134a and/or HFC-134. The purified HFC-134a and/or HFC-134 can be substantially free of its isomer. The substantially free tetrafluoroethane is also typically substantially pure. By "substantially pure" or "purified" it is meant that the recovered tetrafluoroethane is at least about 99% pure tetrafluoroethane on a weight percent basis.

In one aspect of the invention, an extractive agent, e.g. methanol, is introduced at an upper feed point of an extractive distillation column, whereas the first mixture requiring separation, e.g., comprising HFC-134 and HFC-134a, is introduced at a relatively lower point in the column. The liquid extractive agent passes downwardly through trays which are located in the center of the column and contacts the first mixture thereby forming a second mixture. While in the presence of the extractive agent, HFC-134a is relatively more volatile than HFC-134, thereby allowing HFC-134a substantially free of HFC-134 to exit the top of the column. The HFC-134a, which is exiting the top of the column, can be condensed by using conventional reflux condensers. At least a portion of this condensed stream can be returned to the top of the column as reflux, and the remainder recovered as a useful product, e.g., substantially pure HFC-134a. If desired, the HFC-134a can be transported to a second extractive distillation column and/or a second conventional distillation column for further purification. For example, the recovered HFC-134a can be transported to a second extractive distillation column for removing fluorocarbon impurities.

HFC-134, extractive agent and other fluorocarbon impurities comprise a third mixture that exits from the bottom of the column which can in turn then be passed to a stripper or conventional distillation column for separation by using conventional distillation or other known methods. If desired, the extractive agent may then be recycled to the extractive distillation column. In some cases, the HFC-134 is separated from the extractive agent and recovered as a useful product, e.g., the extractive agent can be removed from the HFC-134 by using conventional distillation. The recovered HFC-134 can also be transported to a second or third conventional and/or extractive distillation column for removing fluorocarbon impurities, thereby obtaining substantially pure HFC-134.

If desired, the extractive agent can be removed by any other expedient method such as water extraction. For example, a mixture of HFC-134a or HFC-134 and alcohol is passed through water whereby the alcohol is preferentially withdrawn from the mixture.

Depending upon the quantity of HFC-134a and HFC-134 in the first mixture, HFC-134 can be removed from a mixture containing relatively large quantities of HFC-134a, or vice versa, thereby producing the desired tetrafluoroethane which is substantially free of its isomer.

The ratio of the material exiting the top of the extractive distillation column, which is then condensed and in turn returned to the column, to the amount of material that is removed as product is commonly referred to as the reflux ratio. The reflux ratio will define the physical characteristics of the extractive distillation column. In general, an increase in the reflux ratio will in turn cause an increase in the purity of the recovered HFC-134a, e.g., the quantity of extractant in the recovered HFC-134a can be reduced if not eliminated.

The specific conditions that can be used for practicing the invention depend upon a number of interrelated design parameters such as the diameter of the column, selected feed points, the number of separation stages in the column, among other parameters. The operating pressure of the distillation system may range from about 15 to 350 psia, normally about 50 to 300 psia. Typically, an increase in the extractant feed rate relative to the mixture to be separated, or an increase in the reflux ratio will result in an increase in the purity of the overhead product produced. The temperature and heat transfer area of the overhead condenser is normally sufficient to substantially fully condense the overhead product, or is optionally sufficient to achieve the desired reflux ratio by partial condensation.

The temperature that is employed at a given step in the inventive process is a function of the pressure and the design characteristics of the distillation column, e.g., the ratio of extractive agent to the first mixture. Typically, the temperature will range from about −25° to about 200° C. based upon an operating pressure of about 200 psia.

The quantity of fluorocarbon impurities in the first mixture, i.e., the mixture containing HFC-134a and/or HFC-134, can be reduced by using conventional distillation. While conventional distillation processes are incapable of producing HFC-134a or HFC-134 that is substantially free of its isomer, conventional distillation can be used for reducing the initial quantity of other fluorocarbon impurities. For example, conventional distillation can be used for removing relatively large or bulk quantities of impurities, for example, trichlorotrifluoroethane (CFC-113) from the first mixture which in turn is processed in accordance with the inventive process for separating HFC-134a and HFC-134.

The effective amount of the extractive agent can vary widely. In general, however, using an increased amount of extractive agent will enhance the purity of the recovered tetrafluoroethane. Typically, the ratio of extractive agent to tetrafluoroethane ranges from about 2.0 to about 10:1 on a weight basis; however, higher ratios can be employed as needed.

Certain aspects of the invention can be better understood by reference to the figures. Referring now to the Figures, FIG. 1 schematically illustrates a system which can be used for performing one aspect of the inventive distillation process. A first mixture comprising HFC-134a with HFC-134, HCFC-31 and HCFC-1122 as impurities is supplied via conduit 1 to extraction column 2. At least one liquid extractive agent is supplied via conduit 3 to the extraction column 2, and introduced into column 3 at a location above the mixture 1. A second mixture comprising the extractive agent(s), HFC-134, HCFC-31, HCFC-1122, among other fluorocarbon impurities, is removed from the bottom of column 2 and transported to steam-heated reboiler 4. In some cases, the reboiler 4 is attached to the extractive column 2. The second mixture is supplied via conduit 5 to a feed tank 6. Supplemental liquid extractive agent is also supplied to feed tank 6 via conduit 7 thereby forming a third mixture or extractive agent recycle. A pump 8 transports the third mixture to a stripping mixture column 9. Stripping column 9 separates the extractive agents from non-extractive agents. Extractive agent is removed from column 9 and supplied to a second steam heated reboiler 10. In some cases, the reboiler 10 is attached to column 9. Pump 11 transports the extractive agent from the reboiler 10 through a cold water chiller 12, and then to chiller 13. If necessary, excess quantities of extractive agent can be purged prior to reaching chiller 12. Typically, chiller 13 is operated at a temperature of about −25° C. After exiting chiller 13, the extraction agent is supplied via conduit 3 into extraction column 2.

HFC-134 exits from the top of stripping column 9 as an off gas, and is introduced into condenser 14, which is typically operated at a temperature of about −25° C. While under reflux conditions, pump 15 returns a portion of the HFC-134 to the stripping column 9. The remaining portion of the HFC-134 can be removed from the system via conduit 16.

An off gas is also removed from extraction column 2. The off gas can be HFC-134a that is substantially free of HFC-134 and other fluorocarbon impurities. The HFC-134a product is transported via conduit 17 to condenser 18. Condenser 18 is typically operated at a temperature of about −25° C. While under reflux conditions, pump 19 returns a portion of the HFC-134a product to extraction column 2. The HFC-134a product can be removed from the system via conduit 20.

If desired, a second aspect of the inventive process can be practiced by transporting the product from conduit 16 and/or 20, as shown in FIG. 1, to a third column. The third column can be either conventional or extractive distillation column depending upon the composition of the product. For example, the first mixture in conduit 1 may comprise HFC-134a and one or more impurities selected from HFC-134, HCFC-31, HCFC-1122, CFC-12, and CFC-115. The product in conduit 20 comprises HFC-134a, CFC-12 and CFC-115. The second mixture, which has exited extractive distillation column 2, in conduit 5 comprises HFC-134, extractive agent, HCFC-31 and HCFC-1122. The product in conduit 16 comprises HFC-134, HCFC-31, and HCFC-1122. The products in conduits 16 and/or 20 may be transported to a third column for removal of either additional or remaining halocarbon impurities.

In a third aspect of the invention, a system is operated in substantially the same manner as the system in FIG. 1 with the exception that the first mixture in conduit 1 comprises HFC-134 and one or more impurities selected from HFC-134a, HFC-152a, CFC-115, and CFC-12. In this system, the desired product exits the bottom of extractive distillation column 2 as a mixture of HFC-134/methanol. The mixture of HFC-134/methanol is transported via conduit 5 to distillation column 9 for separating HFC-134 and methanol. In some cases, the product stream in conduit 16 and/or 20 is transported to a third conventional or extractive distillation column for removal of either additional or remaining halocarbon impurities.

While the best results are normally obtained by operating the inventive process at process conditions that minimize formation of azeotropic or azeotrope-like compositions, such compositions may be used to purify HFC-134a and/or HFC-134. The azeotropic or azeotrope-like compositions that can be formed include one or more of the following mixtures: 1,1,1,2 tetrafluoroethane (HFC-134a) and dichlorodifluoromethane (CFC-12); 1,1,1,2 tetrafluoroethane (HFC-134a) and chloropentafluoroethane (CFC-115); 1,1,1,2 tetrafluoroethane (HFC-134a) and chloro-1,1-difluoroethylene (HCFC-1122); chloropentafluoroethane (CFC-115) and 1,1,2,2 tetrafluoroethane (HFC-134); 1,1,2,2 tetrafluoroethane (HFC-134) and 1-chloro-1,1,2,2-tetrafluoroethane (HCFC-124a); 1,1-difluoroethane (HFC-152a) and 1,1,2,2 tetrafluoroethane (HFC-134); among others.

Whenever used in the specification and appended claims the terms below are intended to have the following definitions.

By "azeotrope" or "azeotropic" composition is meant a constant boiling liquid admixture of two or more substances that behaves as a single substance. One way to characterize an azeotropic composition or mixture is that the vapor produced by partial evaporation or distillation of the liquid has the same composition as the liquid from which it was evaporated or distilled, e.g., the admixture distills/refluxes without compositional change. Constant boiling compositions are characterized as azeotropic because they exhibit either a maximum or minimum boiling point, as compared with that of the non-azeotropic mixtures of the same components. An azeotropic composition can also be characterized as the maximum or minimum vapor pressure for a mixture at a given temperature when plotted as a function of mole fraction.

By "azeotrope-like" composition is meant a constant boiling, or substantially constant boiling, liquid admixture of two or more substances that behaves as a single substance. One way to characterize an azeotrope-like composition is that the vapor produced by partial evaporation or distillation of the liquid has substantially the same composition as the liquid from which it was evaporated or distilled, e.g., the admixture distills/refluxes without substantial compositional change. An azeotrope-like composition can also be characterized by the area, which is shown by plotting vapor pressure at given temperature as a function of mole fraction, that is adjacent to the maximum or minimum vapor pressure.

Typically, a composition is azeotrope-like, if, after about 50 weight percent of the composition is removed such as by evaporation or boiling off, the change between the original composition and the composition remaining is less than about 6% and normally less than about 3% relative to the original composition.

By "effective amount" is intended to refer to the amount of each component of the inventive compositions which, when combined, results in the formation of an azeotropic or azeotrope-like composition. This definition includes the amounts of each component, which amounts may vary depending on the pressure applied to the composition so long as the azeotropic or azeotrope-like compositions continue to exist at the different pressures, but with possible different boiling points. Effective amount also includes the amounts, such as may be expressed in weight percentages, of each component of the compositions of the instant invention which form azeotropic or azeotrope-like compositions at temperatures or pressures other than as described herein. Therefore, included in this invention are azeotropic or azeotrope-like compositions consisting essentially of effective amounts of at least one of HFC-134a and/or HFC-134 and at least one fluorinated molecule such that after about 50 weight percent of an original composition is evaporated or boiled off to produce a remaining composition, the change between the original composition and the remaining composition is typically no more than about 6% and normally no more than about 3% or less relative to the original composition.

It is possible to characterize, in effect, a constant boiling admixture which may appear under many guises, depending upon the conditions chosen, by any of several criteria:

* The composition can be defined as an azeotrope of HFC-134a ("A") and a fluorinated halocarbon ("B"), or of HFC-134 ("C") and a fluorinated halocarbon ("D"), among others, because the term "azeotrope" is at once both definitive and limitative, and requires effective amounts of A,B (or C, D) for this unique composition of matter which can be a constant boiling composition.

* It is well known by those skilled in the art, that, at different pressures, the composition of a given azeotrope will vary at least to some degree, and changes in pressure will also change, at least to some degree, the boiling point temperature. Thus, an azeotrope of HFC-134a ("A") and a fluorinated halocarbon ("B") or of HFC-134 ("C") and a fluorinated halocarbon ("D"), among others, represents a unique type of relationship but with a variable composition which depends on temperature and/or pressure. Therefore, compositional ranges, rather than fixed compositions, are often used to define azeotropes.

* The composition can be defined as a particular weight percent relationship or mole percent relationship of HFC-134a ("A") and a fluorinated halocarbon ("B") or of HFC-134 ("C") and a fluorinated halocarbon ("D"), among others, while recognizing that such specific values point out only one particular relationship and that in actuality, a series of such relationships, represented by A,B (or C, D) actually exist for a given azeotrope, varied by the influence of pressure.

* An azeotrope of HFC-134a ("A") and a fluorinated halocarbon ("B") or of HFC-134 ("C") and a fluorinated halocarbon ("D"), among others, can be characterized by defining the compositions as an azeotrope characterized by a boiling point at a given pressure, thus giving identifying characteristics without unduly limiting the scope of the invention by a specific numerical composition, which is limited by and is only as accurate as the analytical equipment available.

The azeotrope or azeotrope-like compositions of the present invention may be formed by operating a conventional distillation apparatus, when practicing the inventive extractive distillation method, and by combining effective amounts of the components by any convenient method including mixing, combining, among others. For best results, a preferred method is to weigh the desired component amounts, and thereafter combine them in an appropriate container.

HFC-134a and HFC-134 can be purified by using the above-identified azeotropic and azeotrope-like compositions in a process that comprises using these azeotropic and azeotrope-like compositions in a conventional distillation method. For example, the conventional distillation column is operated at a temperature and pressure which causes these azeotropes to form. Depending upon whether the azeotropic or azeotrope-like composition has a maximum or minimum boiling point, the composition will be collected, respectively, in the bottoms or as an overhead product. For example, an azeotropic or azeotrope-like composition consisting essentially of, for example, HFC-134a/HCFC-1122 or HFC-134a/CFC-12 is collected as an overhead product whereas a composition consisting essentially of HFC-152a/HFC-134 is collected in the bottoms of the conventional distillation column. In the case of an overhead composition, the azeotropic or azeotrope-like composition can be collected and condensed. In either case, the recovered azeotropic or azeotrope-like composition contains a tetrafluoroethane and a fluorinated halocarbon impurity. The recovered composition, if desired, can be used as the first mixture or feed stream that is processed in accordance with the inventive process described above, e.g., the azeotropic distillation can be used for removing bulk quantities of a fluorocarbon impurity wherein the azeotrope is in turn separated by using extractive distillation.

The following Examples are provided to illustrate certain aspects of the present invention; but not limit the scope of the appended claims. Parts per million (ppm) concentrations are by weight of fluorocarbons, i.e. are given on an extractant-free basis, unless specified otherwise. The following Examples employ the NRTL interaction parameters identified above. In the following Examples, each stage is based upon a 100% operational or performance efficiency. Differing column designs and operating conditions are employed in the extractive distillation than in the Comparative Example in order to maximize the performance of each distillation method. Each Comparative Example shows a conventional distillation and is followed immediately by an Example which shows using the extractive distillation of the invention being applied to the same starting composition. In all examples, the column condenser is counted as stage no. 1.

COMPARATIVE EXAMPLE 1

In this comparative example, conventional distillation within a column with 62 stages is used for purifying a 2,000

Lb/hr feed stream containing 50% by weight of HFC-134 and 50% HFC-134a. The feed is introduced on stage 40 at a temperature of −5 degrees C., with the column condenser pressure at 34.7 psia and the column base pressure 3 psi higher. The distillate temperature is −5.1 degrees C., and the bottom column temperature varies from 0.1 to 3.4 degrees C. depending on the reflux flow. Under these operating conditions, the HFC-134a product will leave in the overhead (distillate) stream from the column. The HFC-134 product exits in the bottoms stream. Conditions are set so as to meet a composition of 100 parts per million (ppm) of HFC-134 in the HFC-134a overhead product, and the reflux flow is varied to show the effect on HFC-134a product recovery and HFC-134 final stream purity.

The results of using this conventional distillation method are shown below in Table 4.

TABLE 4

| Reflux Flow Lb/hr | HFC-134a in Overhd Lb/hr | HFC-134 in Overhd ppm | HFC-134 in Bottom Lb/hr | HFC-134a in Bottom Lb/hr | HFC-134a Recovery % |
| --- | --- | --- | --- | --- | --- |
| 20000 | 100 | 178 | 1000 | 900 | 10.0 |
| 40000 | 132 | 100 | 1000 | 868 | 13.2 |
| 60000 | 565 | 100 | 1000 | 435 | 56.5 |
| 80000 | 802 | 100 | 1000 | 198 | 80.2 |
| 100000 | 881 | 100 | 1000 | 119 | 88.1 |
| 150000 | 934 | 100 | 1000 | 66 | 93.4 |

In order to recover 93% of the HFC-134a at the desired purity, a reflux flow greater than 150,000 lbs/Hr. is necessary. The HFC-134 exiting the bottom of the distillation column would require further purification to possess a purity commensurate with the recovered HFC-134a.

EXAMPLE 1

In this example of the invention, an extractive distillation column with 67 stages is used for purifying a 2000 Lb/hr feed stream containing 50% by weight of HFC-134 and 50% HFC-134a. The feed is introduced on stage 50 and the methanol extractant on stage 15, both at a temperature of −5 degrees C., with the column condenser pressure at 34.7 psia and the column base pressure 3 psi higher. The distillate temperature is −5.1 degrees C., and the bottom column temperature varies from 82 to 87 degrees C. depending of the extractant flow. Under these operating conditions, the HFC-134a product will leave in the overhead (distillate) stream from the column. The HFC-134 product exits in the bottoms stream with methanol. Conditions are set so as to meet a composition of 10 parts per million (ppm) of HFC-134 in the HFC-134a overhead product, and the extractant feed rate is varied to show the effect on bottom product purity.

The results of using this inventive extractive distillation process are shown below in Table 5.

TABLE 5

| Extract. Flow Lb/hr | Reflux Flow Lb/hr | HFC-134a in Overhd Lb/hr | HFC-134 in Overhd ppm | HFC-134 in Bottom Lb/hr | HFC-134a in Bottom ppm | HFC-134a Recovery % |
| --- | --- | --- | --- | --- | --- | --- |
| 20000 | 9000 | 1000 | 10 | 1000 | 26 | 100 |
| 25000 | 9000 | 1000 | 10 | 1000 | 20 | 100 |
| 30000 | 9000 | 1000 | 10 | 1000 | 16 | 100 |
| 35000 | 9000 | 1000 | 10 | 1000 | 13 | 100 |

Table 5 shows that by using methanol as an extractive distillation agent, both the overhead and bottom products are substantially pure, i.e., the products contain 10 to 13 ppm impurities, and the recovery of each is about 100%. In this example, the overhead stream contains less than 0.01 ppm of methanol that, if desired, can be removed by water extraction.

In Comparative Example 1, the impurity level is by comparison 100 ppm in the overhead and 6.6% (66,000 ppm) in the bottom.

COMPARATIVE EXAMPLE 2

In this comparative example, conventional distillation is performed in a column with 62 stages for purifying a 1005 Lb/hr feed stream containing 1000 Lb/hr of HFC-134 and 5 Lb/hr of HFC-152a (a nominal concentration of 5000 ppm). The feed is introduced on stage 25 at a temperature of −5 degrees C., with the column condenser pressure at 34.7 psia and the column base pressure 3 psi higher. The distillate temperature is 1.7 degrees C., and the bottom column temperature is 4.0 degrees C.

The results of this distillation process are shown below in Table 6. The goal is to remove HFC-152a in the bottoms along with as much HFC-134 as necessary to obtain pure HFC-134 as an overhead product.

TABLE 6

| Reflux Flow Lb/hr | HFC-152a in Overhd Lb/hr | HFC-134 in Overhd Lb/hr | HFC-152a in Bottom ppm | HFC-134 in Bottom Lb/hr | HFC-134 Recovery % |
| --- | --- | --- | --- | --- | --- |
| 20000 | 0.83 | 385 | 6726 | 615 | 62 |
| 50000 | 0.65 | 385 | 7029 | 615 | 61 |
| 100000 | 0.57 | 385 | 7155 | 615 | 61 |

Table 6 illustrates that conventional distillation is ineffective for separating these compounds. The recovery effeciency is limited because an azeotrope is formed between HFC-152a and HFC-134. However, this Example illustrates how the concentration of HFC-152a can be reduced from a first mixture comprising HFC-152a and HFC-134 by using azeotropic distillation.

EXAMPLE 2

In this example of the inventive process, extractive distillation is performed in an extractive distillation column with 57 stages for purifying the same feed stream as in Comparative Example 2. The feed is introduced on stage 40 and the methanol extractant on stage 15, both at a temperature of −5 degrees C., with the column condenser pressure at 34.7 psia and the column base pressure 3 psi higher. The distillate temperature is −3.1 degrees C., and the bottom column temperature varies from 82 to 86 degrees C. depending on the extractant flow rate. Under these operating conditions, the HFC-134 product will leave in the bottoms stream from the column along with the methanol extractant. Conditions are set so as to meet a composition of 10 parts per million (ppm) of HFC-152a in the HFC-134 bottoms product.

The results of this extractive distillation process are shown below in Table 7.

TABLE 7

| Extract. Flow Lb/hr | Reflux Flow Lb/hr | HFC-152a in Overhd Lb/hr | HFC-134 in Overhd ppm | HFC-152a in Bottom ppm | HFC-134 in Bottom Lb/hr | HFC-134 Recovery % |
|---|---|---|---|---|---|---|
| 20000 | 1000 | 5.0 | 608 | 10 | 1000 | 100 |
| 25000 | 1000 | 5.0 | 26 | 10 | 1000 | 100 |
| 30000 | 1000 | 5.0 | 10 | 10 | 1000 | 100 |

By using methanol as an extractive agent, both the overhead and bottom products are substantially pure. The overhead also contains less than 0.01 ppm methanol that can be removed, if desired, by water extraction.

COMPARATIVE EXAMPLE 3

In this comparative example, conventional distillation is performed in the column described in Comparative Example 2 for purifying a 1005 Lb/hr feed stream containing 1000 Lb/hr of HFC-134 and 5 Lb/hr of HCFC-124a (a nominal concentration of 5000 ppm). The feed is introduced on stage 25 at a temperature of −5 degrees C., with the column condenser pressure at 34.7 psia and the column base pressure 3 psi higher. The distillate temperature is 1.7 degrees C., and the bottom column temperature is 4 degrees C.

The results of this conventional distillation process are shown below in Table 8. The goal is to remove HCFC-124a as an overhead product along with HFC-134 as necessary to obtain pure HFC-134 in the bottoms.

TABLE 8

| Reflux Flow Lb/hr | HCFC-124a in Overhd Lb/hr | HFC-134 in Overhd Lb/hr | HCFC-124a in Bottom ppm | HFC-134 in Bottom Lb/hr | HFC-134 Recovery % |
|---|---|---|---|---|---|
| 20000 | 3.5 | 498 | 3431 | 502 | 50 |
| 50000 | 3.4 | 497 | 3113 | 503 | 50 |
| 100000 | 3.3 | 497 | 2987 | 503 | 50 |

By using the reflux ratios shown in Table 8, HCFC-124a is not effectively separated from the mixture. The recovery effeciency is limited because an azeotrope is formed between HFC-134a and HCFC-124a. However, this Example illustrates how the concentration of HCFC-124a can be reduced from a first mixture comprising HFC-134a and HCFC-124a by using azeotropic distillation.

EXAMPLE 3

In this example of the invention, extractive distillation is performed in a column with 57 stages for purifying the same feed stream as in Comparative Example 3. The feed and methanol extractant are fed at the same conditions as Example 2. The distillate temperature is 1.7 degrees C., and the bottom column temperature varies from 88 to 90 degrees C. depending on the extractant flow rate. Under these operating conditions, the HFC-134 product will leave in the overhead stream from the column. Conditions are set so as to meet a composition of 10 parts per million (ppm) of HCFC-124a in the HFC-134 distillate product, and the extractant feed rate is varied to show the effect on bottoms composition.

The results of this extractive distillation process are shown below in Table 9.

TABLE 9

| Extract. Flow Lb/hr | Reflux Flow Lb/hr | HCFC-124a in Overhd ppm | HFC-134 in Overhd Lb/hr | HCFC-124a in Bottom Lb/hr | HFC-134 in Bottom Lb/hr | HFC-134 Recovery % |
|---|---|---|---|---|---|---|
| 5000 | 1000 | 11 | 919 | 5.0 | 81 | 92 |
| 7500 | 1000 | 10 | 1000 | 5.0 | 0.3 | 100 |
| 10000 | 1000 | 10 | 1000 | 5.0 | 0.07 | 100 |

By using methanol as an extractive agent at a 7500 Lb/hr flowrate or higher, a composition of substantially pure HFC-134 is obtained overhead with approximately 100% recovery. The overhead also contains a relatively small amount of methanol, e.g., varying from 0.9 to 1.3 ppm, that can be removed, if desired, by water extraction.

COMPARATIVE EXAMPLE 4

In this comparative example, conventional distillation is performed in the column and feed conditions described in Comparative Example 2 for purifying a 1005 Lb/hr feed stream containing 1000 Lb/hr of HFC-134 and 5 Lb/hr of CFC-115 (a nominal concentration of 5000 ppm). The distillate temperature is −19 degrees C., and the bottom column temperature is 4 degrees C. Under these operating conditions, the HFC-134 product will leave in the bottoms stream from the column. The CFC-115 impurity exits in the overhead stream as an azeotrope with the HFC-134.

The results of this conventional distillation process are shown below in Table 10.

TABLE 10

| Reflux Flow Lb/hr | CFC-115 in Overhd Lb/hr | HFC-134 in Overhd ppm | CFC-115 in Bottom ppm | HFC-134 in Bottom Lb/hr | HFC-134 Recovery % |
|---|---|---|---|---|---|
| 1000 | 4.9 | 125000 | 100 | 999 | 99.9 |
| 2500 | 4.9 | 125000 | 100 | 999 | 99.9 |
| 5000 | 4.9 | 125000 | 100 | 999 | 99.9 |

Table 10 shows that a portion of the HFC-134 forms an overhead azeotrope, and that the purity of the overhead CFC-115 is relatively low. The HFC-134 recovery efficiency is limited because an azeotrope is formed between HFC-134 and CFC-115. However, this Example illustrates how the concentration of CFC-115 can be reduced from a first mixture comprising HFC-134 and CFC-115 by using azeotropic distillation.

EXAMPLE 4

In this example of the invention, extractive distillation is performed in the column and feed conditions described in Example 2 for purifying the same feed stream as in Comparative Example 4. The distillate temperature is −18 degrees C., and the bottom column temperature varies from 23 to 49 degrees C. depending of the extractant flow rate. Under these operating conditions, the HFC-134 product will leave in the bottoms stream from the column along with the extractant. Conditions are set so as to meet a composition of 10 parts per million (ppm) of CFC-115 in the HFC-134 bottoms product, and the extractant feed rate is varied to show the effect on overhead composition.

The results of this extractive distillation method are shown below in Table 11.

TABLE 11

| Extract. Flow Lb/hr | Reflux Flow Lb/hr | CFC-115 in Overhd Lb/hr | HFC-134 in Overhd ppm | CFC-115 in Bottom ppm | HFC-134 in Bottom Lb/hr | HFC-134 Recovery % |
|---|---|---|---|---|---|---|
| 1000 | 1000 | 5.0 | <0.01 | 10 | 1000 | 100 |
| 2000 | 1000 | 5.0 | <0.01 | 10 | 1000 | 100 |
| 3000 | 1000 | 5.0 | <0.01 | 10 | 1000 | 100 |

By using methanol as an extractive agent, the separation of CFC-115 and HFC-134 can be improved over Comparative Example 4. While the overhead also contains a relatively small amount of extractant methanol, e.g., varying from 1.5 to 1.8 ppm, such can be removed, if desired, by water extraction.

COMPARATIVE EXAMPLE 5

In this comparative example, conventional distillation is performed in the column and feed conditions described in Comparative Example 2 for purifying a 1005 Lb/hr feed stream containing 1000 Lb/hr of HFC-134 and 5 Lb/hr of CFC-12 (a nominal concentration of 5000 ppm). The distillate temperature is −10 degrees C., and the bottom column temperature is 4 degrees C.

The results of this conventional distillation are shown below in Table 12.

TABLE 12

| Reflux Flow Lb/hr | CFC-12 in Overhd Lb/hr | HFC-134 in Overhd Lb/hr | CFC-12 in Bottom ppm | HFC-134 in Bottom Lb/hr | HFC-134 Recovery % |
|---|---|---|---|---|---|
| 1000 | 4.9 | 1.8 | 100 | 998 | 99.8 |
| 2500 | 4.9 | 1.8 | 100 | 998 | 99.8 |
| 5000 | 4.9 | 1.8 | 100 | 998 | 99.8 |

Table 12 shows that a portion of the HFC-134 forms an overhead azeotrope, and that the purity of the overhead CFC-12 is relatively low.

EXAMPLE 5

In this example of the invention, extractive distillation is performed in the column and feed conditions described in Example 2 for purifying the same feed stream as described in Comparative Example 5. The feed is introduced on stage 40 and the methanol extractant on stage 15. The distillate temperature varies from −6.0 to −7.5 degrees C., and the bottom column temperature varies from 23 to 62 degrees C. depending of the extractant flow rate. Under these operating conditions, the HFC-134 product will leave in the bottoms stream from the column along with the extractant. Conditions are set so as to meet a composition of 1 part per million (ppm) of CFC-12 in the HFC-134 bottoms product, and the extractant feed rate is varied to show the effect on overhead composition.

The results of this extractive distillation are shown below in Table 13.

TABLE 13

| Extract. Flow Lb/hr | Reflux Flow Lb/hr | CFC-12 in Overhd Lb/hr | HFC-134 in Overhd ppm | CFC-12 in Bottom ppm | HFC-134 in Bottom Lb/hr | HFC-134 Recovery % |
|---|---|---|---|---|---|---|
| 1000 | 1000 | 5.0 | >10000 | 45 | 999 | 99.9 |
| 2000 | 1000 | 5.0 | <0.01 | 1 | 1000 | 100.0 |
| 3000 | 1000 | 5.0 | <0.01 | 1 | 1000 | 100.0 |
| 4000 | 1000 | 5.0 | <0.01 | 1 | 1000 | 100.0 |
| 5000 | 1000 | 5.0 | <0.01 | 1 | 1000 | 100.0 |

By using methanol as an extractive agent, CFC-12 and HFC-134 can be substantially completely separated. While the overhead also contains a relatively small amount of methanol, e.g., varying from 0.01 to 0.04 ppm, such an amount can be removed, if desired, by water extraction.

COMPARATIVE EXAMPLE 6

In this comparative example, conventional distillation in a performed in a column with 62 stages for purifying a 1333 Lb/hr feed stream containing 1000 Lb/hr of HFC-134a and 333 Lb/hr of CFC-12 (a nominal concentration of 25%). The feed is introduced on stage 25 at a temperature of −5 degrees C., with the column condenser pressure at 34.7 psia and the column base pressure 3 psi higher. The distillate temperature is −13 degrees C., and the bottom column temperature is −3 degrees C.

The results of this conventional distillation are shown below in Table 14.

TABLE 14

| Reflux Flow Lb/hr | CFC-12 in Overhd Lb/hr | HFC-134a in Overhd Lb/hr | CFC-12 in Bottom ppm | HFC-134a in Bottom Lb/hr | HFC-134a Recovery % |
|---|---|---|---|---|---|
| 2000 | 333 | 214 | 10 | 786 | 78.6 |
| 3000 | 333 | 214 | 10 | 786 | 78.6 |
| 5000 | 333 | 214 | 10 | 786 | 78.6 |
| 10000 | 333 | 214 | 10 | 786 | 78.6 |

While HFC-134a can be recovered in the overhead, the recovery rate and purity are relatively low. The HFC-134a recovery efficiency is limited because an azeotrope is formed between HFC-134a and CFC-12. However, this Example illustrates how the concentration of CFC-12 can be reduced from a first mixture comprising HFC-134a and CFC-12 by using azeotropic distillation.

EXAMPLE 6

In this example of the invention, extractive distillation is performed in a column with 57 stages for purifying the same feed stream as described in Comparative Example 6. The feed and methanol extractant are introduced at the same conditions and locations as described in Example 2. The distillate temperature varies from −12 to −7.5 degrees C., and the bottom column temperature varies from 48 to 77 degrees C. depending on the extractant flow rate. Under these operating conditions, the HFC-134a product will leave in the bottoms stream from the column along with the extractant. Conditions are set so as to meet a composition of 10 parts per million (ppm) of CFC-12 in the HFC-134 bottoms product, and the extractant feed rate is varied to show the effect on overhead composition.

The results of this extractive distillation process are shown below in Table 15.

TABLE 15

| Extract. Flow Lb/hr | Reflux Flow Lb/hr | CFC-12 in Overhd Lb/hr | HFC-134a in Overhd ppm | CFC-12 in Bottom ppm | HFC-134a in Bottom Lb/hr | HFC-134a Recovery % |
|---|---|---|---|---|---|---|
| 5000 | 1000 | 333 | >10000 | 31 | 944 | 94.4 |
| 7500 | 1000 | 333 | >10000 | 10 | 987 | 98.7 |
| 10000 | 1000 | 333 | 36 | 10 | 1000 | 100 |
| 20000 | 1000 | 333 | 3 | 10 | 1000 | 100 |

By using methanol as an extractive agent, CFC-12 and HFC-134a are substantially completely separated. While the overhead also contains a relatively small amount of methanol, e.g., varying from 0.34 to 0.97 ppm, such an amount can be removed, if desired, by water extraction.

COMPARATIVE EXAMPLE 7

In this comparative example, conventional distillation is performed in the column and feed conditions described in Comparative Example 2, for purifying a 1005 Lb/hr feed stream containing 1000 Lb/hr of HFC-134a and 5 Lb/hr of HCFC-31 (a nominal concentration of 5000 ppm). The distillate temperature is −5 degrees C., and the bottom column temperature is −2.4 to −2.9 degrees C. depending on reflux rate.

The results of the conventional distillation are shown below in Table 16.

TABLE 16

| Reflux Flow Lb/hr | HCFC-31 in Overhd ppm | HFC-134a in Overhd Lb/hr | HCFC-31 in Bottom Lb/hr | HFC-134a in Bottom Lb/hr | HFC-134a Recovery % |
|---|---|---|---|---|---|
| 20000 | 23 | 500 | 5.0 | 500 | 50 |
| 50000 | 10 | 924 | 5.0 | 76 | 92 |

The recovery of HFC-134a as an overhead product was 50%. The recovery of HFC-134a can be increased to about 92% by using a relatively high reflux ratio, e.g., 50 to 1.

EXAMPLE 7

In this example of the invention, extractive distillation is performed in the column and feed conditions described in Example 2 for purifying the same feed stream as in Comparative Example 7. The feed is introduced on stage 40 and the methanol extractant on stage 15. The distillate temperature is −5.1 degrees C., and the bottom column temperature is 90 degrees C. Under these operating conditions, the HFC-134a product will leave in the overhead stream from the column. Conditions are set so as to meet a composition of 10 parts per million (ppm) of HCFC-31 in the HFC-134a overhead product.

The results of the extractive distillation are described below in Table 17.

TABLE 17

| Extract. Flow Lb/hr | Reflux Flow Lb/hr | HCFC-31 in Overhd ppm | HFC-134a in Overhd Lb/hr | HCFC-31 in Bottom Lb/hr | HFC-134a in Bottom Lb/hr | HFC-134a Recovery % |
|---|---|---|---|---|---|---|
| 2000 | 1000 | 10 | 1000 | 5.0 | <0.01 | 100 |

By using methanol as an extractive agent, both the overhead and bottoms are recovered as substantially pure products. The overhead also contains 0.6 ppm methanol that can be removed, if desired, by water extraction.

COMPARATIVE EXAMPLE 8

In this comparative example, conventional distillation is performed in the column described in Comparative Example 4. The feed is the same except that the main ingredient is HFC-134a rather than HFC-134. Operating conditions are also the same except that the distillate temperature is −20 degrees C. and the bottom column temperature is −2.9 degrees C. The HFC-134a product leaves in the bottoms stream from the column, and the CFC-115 impurity exits in the overhead stream as an azeotrope with the HFC-134a.

The results of this conventional distillation are shown in Table 18.

TABLE 18

| Reflux Flow Lb/hr | CFC-115 in Overhd Lb/hr | HFC-134a in Overhd ppm | CFC-115 in Bottom ppm | HFC-134a in Bottom Lb/hr | HFC-134a Recovery % |
|---|---|---|---|---|---|
| 2500 | 4.9 | 183000 | 100 | 999 | 99.9 |
| 5000 | 4.9 | 183000 | 100 | 999 | 99.9 |

Table 18 shows that a portion of the HFC-134a forms an overhead azeotrope, and that the purity of the overhead CFC-115 is relatively low. The recovery efficiency of the HFC-134a is limited because an azeotrope is formed between HFC-134a and CFC-115. However, this Example illustrates how the concentration of CFC-115 can be reduced from a first mixture comprising HFC-134a and CFC-115 by using azeotropic distillation.

EXAMPLE 8

In this example of the invention, extractive distillation is performed in the column and feed conditions described in Example 4 for purifying the same feed stream as in Comparative Example 8. The feed is introduced on stage 40 and the methanol extractant on stage 15. The distillate temperature is −18 degrees C., and the bottom column temperature varies from 10 to 32 degrees C. depending of the extractant flow rate. Under these operating conditions, the HFC-134a product will leave in the bottoms stream from the column along with the extractant. Conditions are set so as to meet a composition of 10 parts per million (ppm) of CFC-115 in the HFC-134a bottoms product, and the extractant feed rate is varied to show the effect on overhead composition.

The results of the extractive distillation are shown below in Table 19.

TABLE 19

| Extract. Flow Lb/hr | Reflux Flow Lb/hr | CFC-115 in Overhd Lb/hr | HFC-134a in Overhd ppm | CFC-115 in Bottom ppm | HFC-134a in Bottom Lb/hr | HFC-134a Recovery % |
|---|---|---|---|---|---|---|
| 1000 | 1000 | 5.0 | <0.01 | 10 | 1000 | 100 |
| 2000 | 1000 | 5.0 | <0.01 | 10 | 1000 | 100 |
| 3000 | 1000 | 5.0 | <0.01 | 10 | 1000 | 100 |

Table 19 shows that by using methanol as extractive agent, HFC-134a can be recovered that is substantially free of CFC-115, and the CFC-115 can be recovered as being substantially free of HFC-134a. While the overhead also contains a relatively small amount methanol, e.g., varying from 1.5 to 1.8 ppm, is amount can be removed, if desired, by water extraction.

COMPARATIVE EXAMPLE 9

In this comparative example, conventional distillation is performed in the column and feed conditions described in Comparative Example 2 for purifying a 1005 Lb/hr feed stream containing 1000 Lb/hr of HFC-134a and 5 Lb/hr of HCFC-1122 (a nominal concentration of 5000 ppm). The distillate temperature is −5.3 to −6.4 degrees C. depending on reflux ratio, and the bottom column temperature is −2.9 degrees C.

The results of this conventional distillation process are shown below in Table 20.

TABLE 20

| Reflux Flow Lb/hr | HCFC-1122 in Overhd Lb/hr | HFC-134a in Overhd Lb/hr | HCFC-1122 in Bottom ppm | HFC-134a in Bottom Lb/hr | HFC-134a Recovery % |
|---|---|---|---|---|---|
| 2000 | 4.6 | 254 | 560 | 746 | 74.6 |
| 3000 | 4.9 | 233 | 100 | 767 | 76.7 |
| 4000 | 4.9 | 43 | 100 | 957 | 95.7 |
| 5000 | 4.9 | 13 | 100 | 987 | 98.7 |

The recovery efficiency of the HFC-134a is limited because an azeotrope is formed between HFC-134a and CFC-115. However, this Example illustrates how the concentration of CFC-115 can be reduced from a first mixture comprising HFC-134a and CFC-115 by using azeotropic distillation.

EXAMPLE 9

In this example of the invention, extractive distillation is performed in a column with 57 stages for purifying the same feed stream as described in Comparative Example 9. The feed is introduced on stage 40 and the methanol extractant on stage 15, both at a temperature of −5 degrees C., with the column condenser pressure at 34.7 psia and the column base pressure 3 psi higher. The distillate temperature is −5.1 degrees C., and the bottom column temperature varies from 88 to 91 degrees C. depending on the extractant flowrate. Under these operating conditions, the HFC-134a product will leave in the overhead stream from the column. Conditions are set so as to meet a composition of 100 parts per million (ppm) of HCFC-1122 in the HFC-134a overhead product.

The results of this extractive distillation process are shown below in Table 21.

TABLE 21

| Extract. Flow Lb/hr | Re-flux Flow Lb/hr | HCFC-1122 in Overhd ppm | HFC-134a in Overhd Lb/hr | HCFC-1122 in Bottom Lb/hr | HFC-134a in Bottom Lb/hr | HFC-134a Recovery % |
|---|---|---|---|---|---|---|
| 10000 | 2000 | 110 | 907 | 4.9 | 93 | 90.7 |
| 15000 | 2000 | 100 | 990 | 4.9 | 10 | 99.0 |
| 20000 | 2000 | 100 | 996 | 4.9 | 4 | 99.6 |
| 25000 | 2000 | 100 | 998 | 4.9 | 2 | 99.8 |

By using methanol as an extractive agent, the product recovery is increased to as high as 99.8%. The overhead also contains up to 0.03 ppm methanol which can be removed, if desired, by water extraction.

The above Examples illustrate that an extractive agent can be employed for separating HFC-134a and HFC-134 from each other and numerous fluorocarbon impurities. In some cases, one or more extractive agents can be used in combination. For example, by using a mixture of extractive agents the inventive process may be maximized to obtain HFC-134a that has the desired purity while minimizing the extractive agent cost. Alternatively, a series of one or more chemically related or distinct extractive agents can be employed for maximizing the effectiveness of the inventive process.

EXAMPLE 10

This Example demonstrates the existence of azeotropic and azeotrope-like compositions between the binary pair mixtures consisting essentially of CFC-115 and HFC-134; HFC-134 and HCFC-124a; HFC-152a and HFC-134; CFC-12 and HFC-134a; CFC-115 and HFC-134a; HFC-134a and HCFC-1122.

To determine the relative volatility of each binary pair, the so-called PTx Method was used. In this procedure, for each binary pair, the total absolute pressure in a PTx cell of known volume was measured at a constant temperature for various known binary compositions. These measurements were then reduced to equilibrium vapor and liquid compositions in the cell using the NRTL equation. Samples of selected vapor and liquid sets were obtained and analyzed to verify their respective compositions.

The vapor pressure measured versus the composition in the PTx cell for the CFC-115/HFC-134; HFC-134/HCFC-124a; HFC-152/HFC-134; CFC-12/HFC-134a; CFC-115/HFC-134a; and HFC-134a/HCFC-112 systems are shown in FIGS. 2 through 7, respectively. The experimental data points are shown in each Figure as solid points on each Figure and the curve is drawn by using computer modeling.

Figure 2:
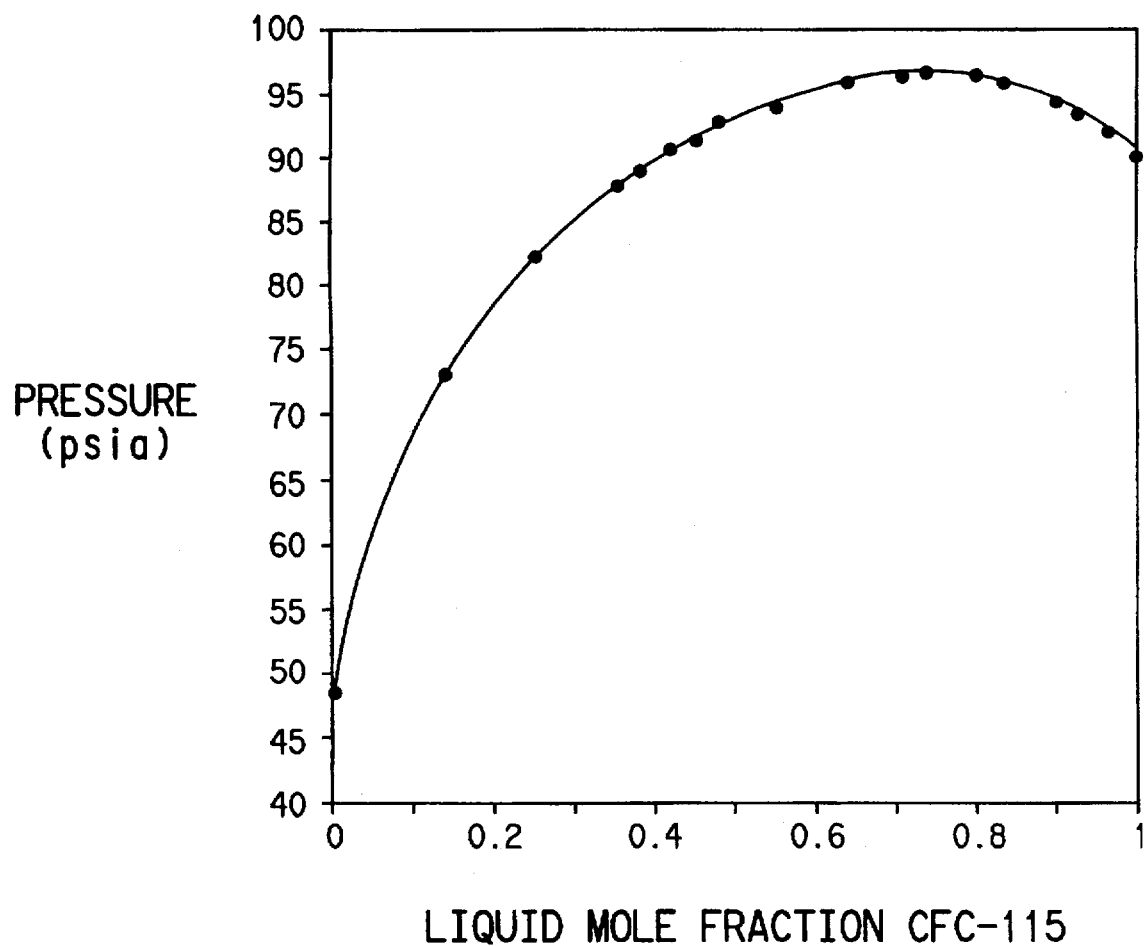
FIG. 2—FIG. 2 is a graphical representation of an azeotropic and azeotrope-like compositions consisting essentially of CFC-115 and HFC-134 at a temperature of about 11.2° C.

Referring now to FIG. 2, FIG. 2 illustrates graphically the formation of an azeotropic and azeotrope-like composition consisting essentially of CFC-115 and HFC-134 at 11.2° C., as indicated by a mixture of about 72.4 mole % CFC-115 and 27.6 mole % HFC-134 having the highest pressure over the range of compositions at this temperature. Based upon these findings, it has been calculated that an azeotropic or azeotrope-like composition of about 93 mole % CFC-115 and 7 mole % HFC-134 is formed at −50° C. and 8.8 psia and an azeotropic or azeotrope-like composition of about 65.9 mole % CFC-115 and about 34.1 mole % HFC-134 is formed at 55° C. and 326 psia. Accordingly, the present invention provides an azeotropic or azeotrope-like composition consisting essentially of from about 65 to about 93 mole % CFC-115 and from about 35 to 7 mole % HFC-134, said composition having a boiling point of from about −50 at 8.8 psia to about 55° C. at 326 psia.

Figure 3:
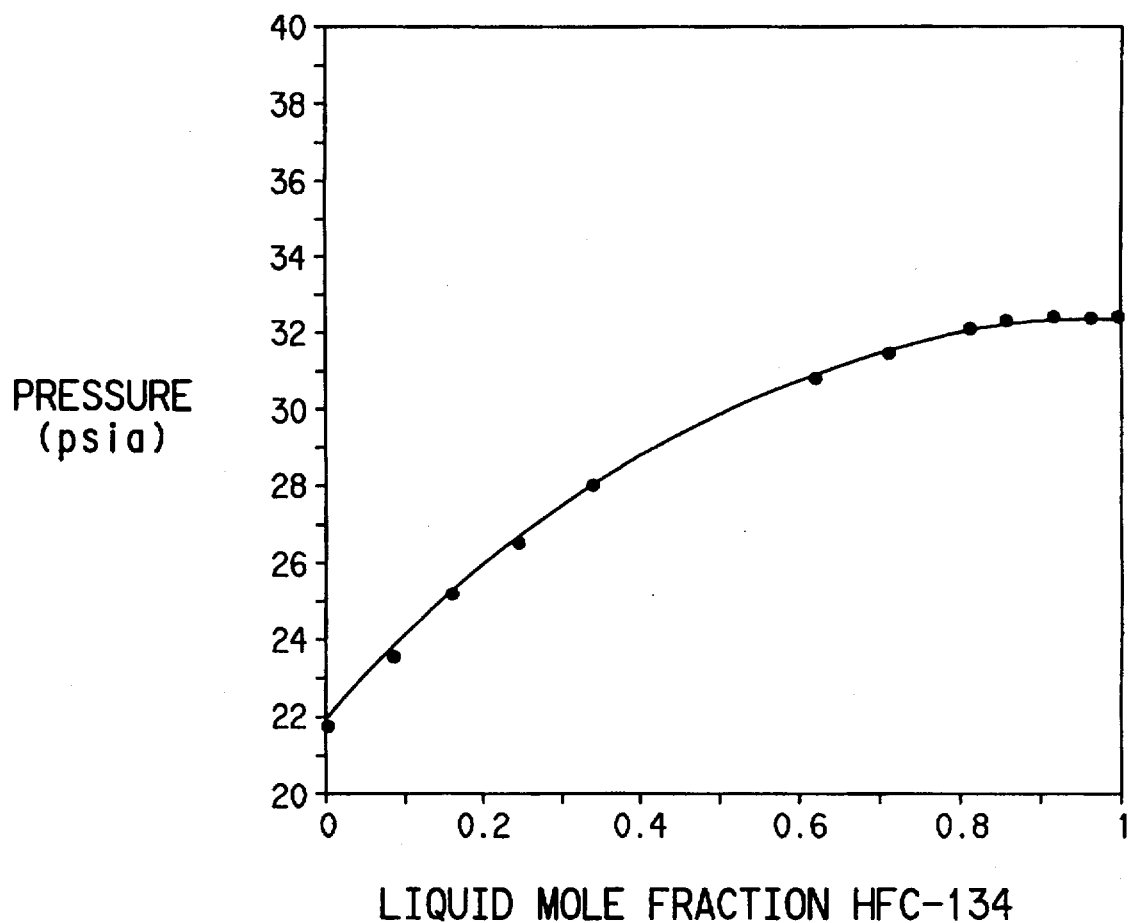
FIG. 3—FIG. 3 is a graphical representation of an azeotropic and azeotrope-like compositions consisting essentially of HFC-134 and HCFC-124a at a temperature of about −0.2° C.

Referring now to FIG. 3, FIG. 3 illustrates graphically the formation of an azeotropic and azeotrope-like composition consisting essentially of HFC-134 and HCFC-124a at −0.2° C., as indicated by a mixture of about 96.9 mole % HFC-134 and 3.1 mole % HCFC-124a having the highest pressure over the range of compositions at this temperature. Based upon these findings, it has been calculated that an azeotropic or azeotrope-like composition of about 99.9 mole % HFC-134 and 0.1 mole % HCFC-124a is formed at −20° C. and 14.4 psia, and an azeotropic or azeotrope-like composition of about 91.9 mole % HFC-134 and 8.1 mole % HCFC-124a is formed at 60° C. and 199 psia. Accordingly, the present invention provides an azeotropic or azeotrope-like composition consisting essentially of from about 91 to about 99.9 mole % HFC-134 and from about 9 to 0.1 mole % HCFC-124a, said composition having a boiling point of from about −20° C. at 14.4 psia to about 60° C. at 199 psia.

Figure 4:
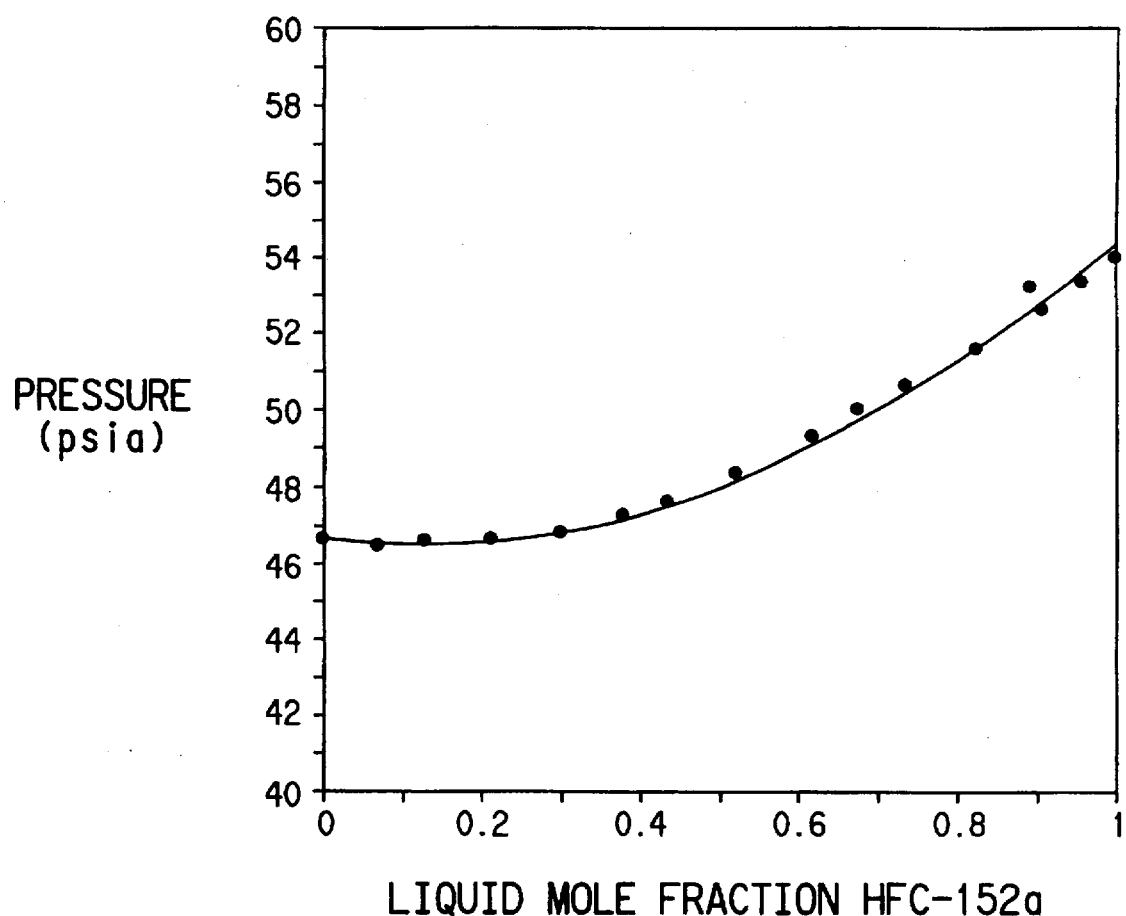
FIG. 4—FIG. 4 is a graphical representation of an azeotropic and azeotrope-like compositions consisting essentially of HFC-152a and HFC-134 at a temperature of about 10° C.

Referring now to FIG. 4, FIG. 4 illustrates graphically the formation of an azeotropic and azeotrope-like composition consisting essentially of HFC-152a and HFC-134 at 10° C., as indicated by a mixture of about 93.7 mole % HFC-134 and 6.3 mole % HFC-152a having the lowest pressure over the range of compositions at this temperature. Based upon these findings, it has been calculated that an azeotropic or azeotrope-like composition of about 99.9 mole % HFC-134 and 0.1 mole % HFC-152a is formed at −25° C. and 11.5 psia and an azeotropic or azeotrope-like composition of about 83.1 mole % HFC-134 and 16.9 mole % HFC-152a is formed at 50° C. and 153 psia. Accordingly, the present invention provides an azeotropic or azeotrope-like composition consisting essentially of from about 83.1 to about 99.9 mole % HFC-134 and from about 16.9 to about 0.1 mole % HFC-152a, said composition having a boiling point of from about −25° C. at 11.5 psia to about 50° C. at 153 psia.

Figure 5:
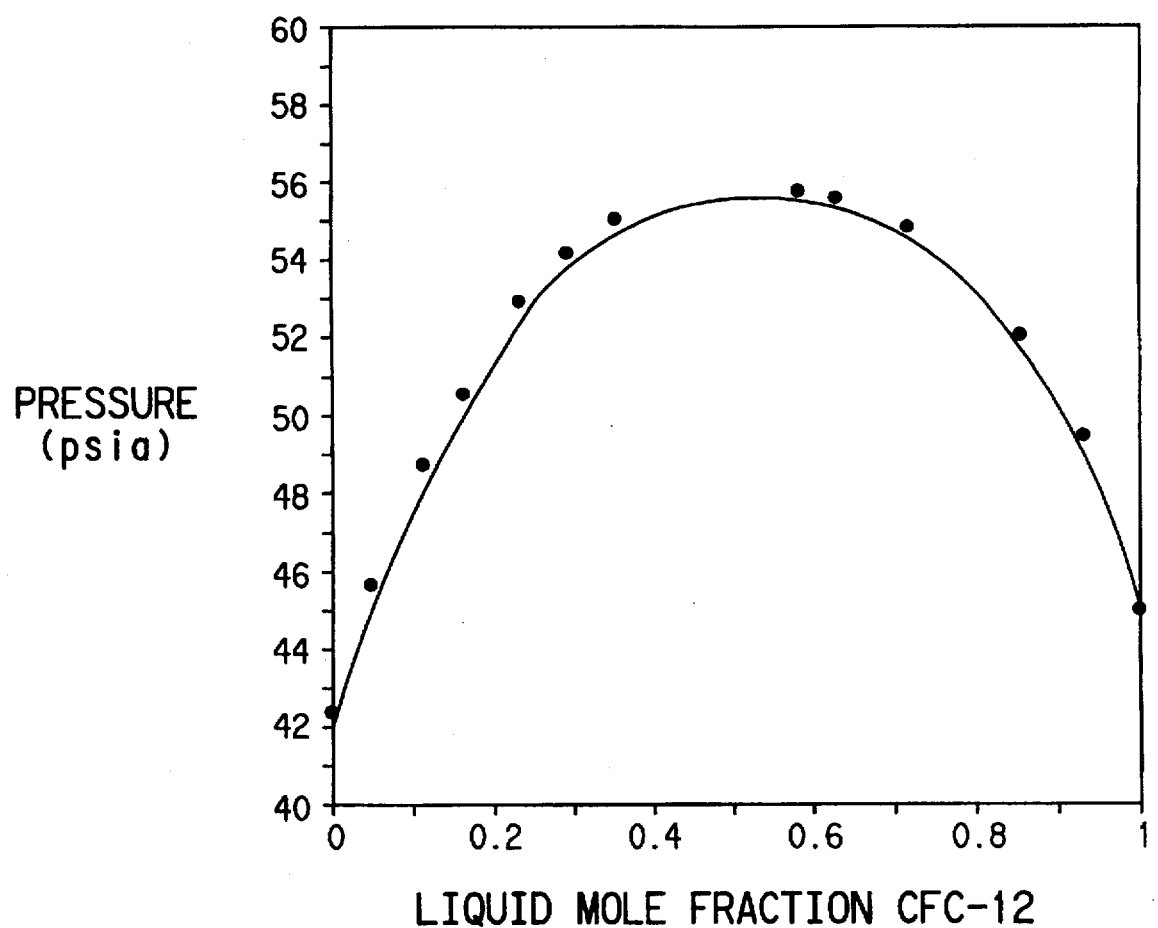
FIG. 5—FIG. 5 is a graphical representation of an azeotropic and azeoptrope-like compositions consisting essentially of CFC-12 and HFC-134a at a temperature of about 0° C.

Referring now to FIG. 5, FIG. 5 illustrates graphically the formation of an azeotropic and azeotrope-like composition consisting essentially of CFC-12 and HFC-134a at 0° C., as indicated by a mixture of about 58.3 mole % CFC-12 and 41.7 mole % HFC-134a having the highest pressure over the range of compositions at this temperature. Based upon these findings, it has been calculated that an azeotropic or azeotrope-like composition of about 62.8 mole % CFC-12 and 37.2 mole % HFC-134a is formed at −50° C. and 6.8 psia and an azeotropic or azeotrope-like composition of about 46.9 mole % CFC-12 and about 53.1 mole % HFC-134a is formed at 50° C. and 235 psia. Accordingly, the present invention provides an azeotropic or azeotrope-like composition consisting essentially of from about 46.9 to about 62.8 mole % CFC-12 and from about 53.1 to about 37.2 mole % HFC-134a, said composition having a boiling point of from about −50° C. at 6.8 psia to about 50° C. at 235 psia.

Figure 6:
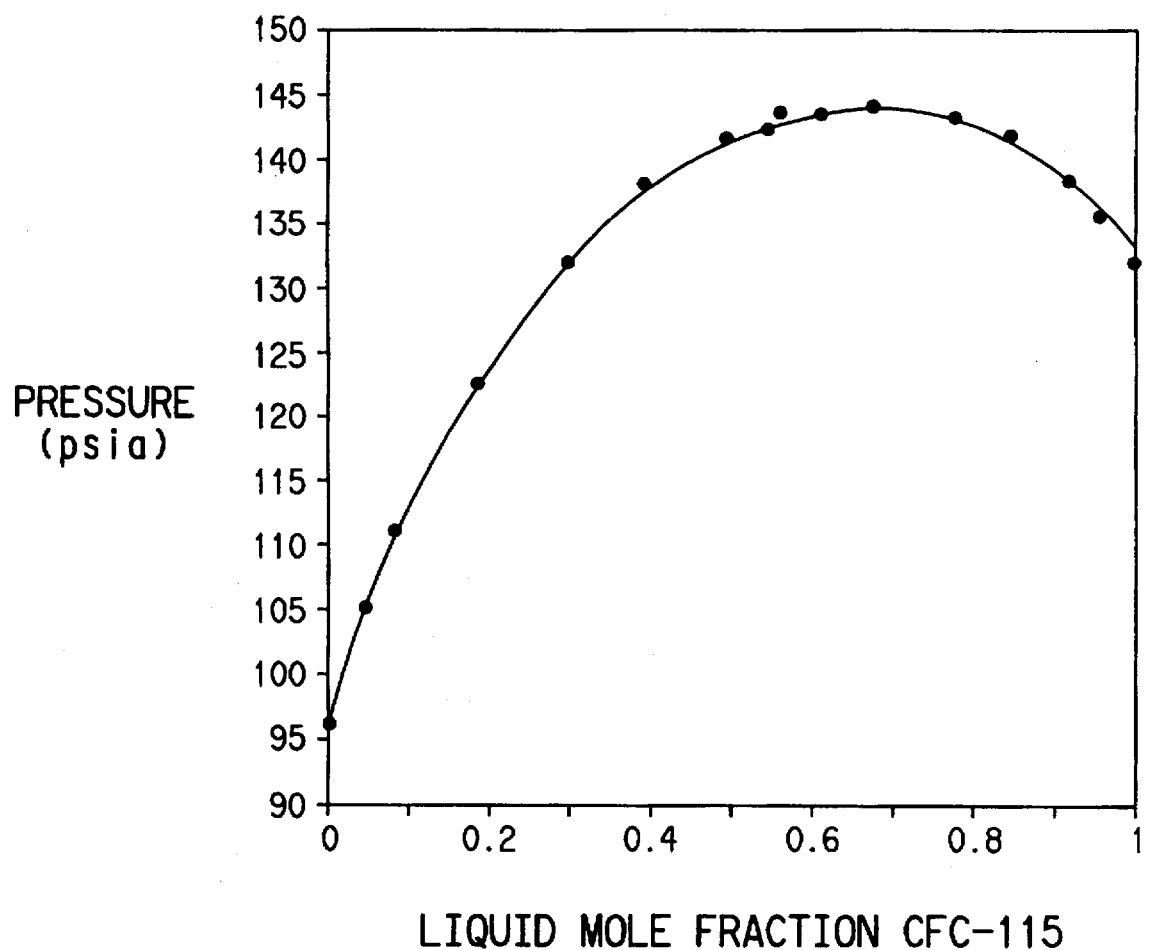
FIG. 6—FIG. 6 is a graphical representation of an azeotropic and azeotrope-like compositions consisting essentially of CFC-115 and HFC-134a at a temperature of about 25° C.

Referring now to FIG. 6, FIG. 6 illustrates graphically the formation of an azeotropic and azeotrope-like composition consisting essentially of CFC-115 and HFC-134a at 25° C., as indicated by a mixture of about 67.9 mole % CFC-115 and 32.1 mole % HFC-134a having the highest pressure over the range of compositions at this temperature. Based upon these findings, it has been calculated that an azeotropic or azeotrope-like composition of about 80.5 mole % CFC-115 and 19.5 mole % HFC-134a is formed at −50° C. and 9.4 psia and an azeotropic or azeotrope-like composition of about 63.1 mole % CFC-115 and about 36.9 mole % HFC-134a is formed at 60° C. and 330 psia. Accordingly, the present invention provides an azeotropic or azeotrope-like composition consisting essentially of from about 63.1 to about 80.5 mole % CFC-115 and from about 36.9 to about 19.5 mole % HFC-134a, said composition having a boiling point of from about −50° C. at 9.4 psia to about 60° C. at 330 psia.

Figure 7:
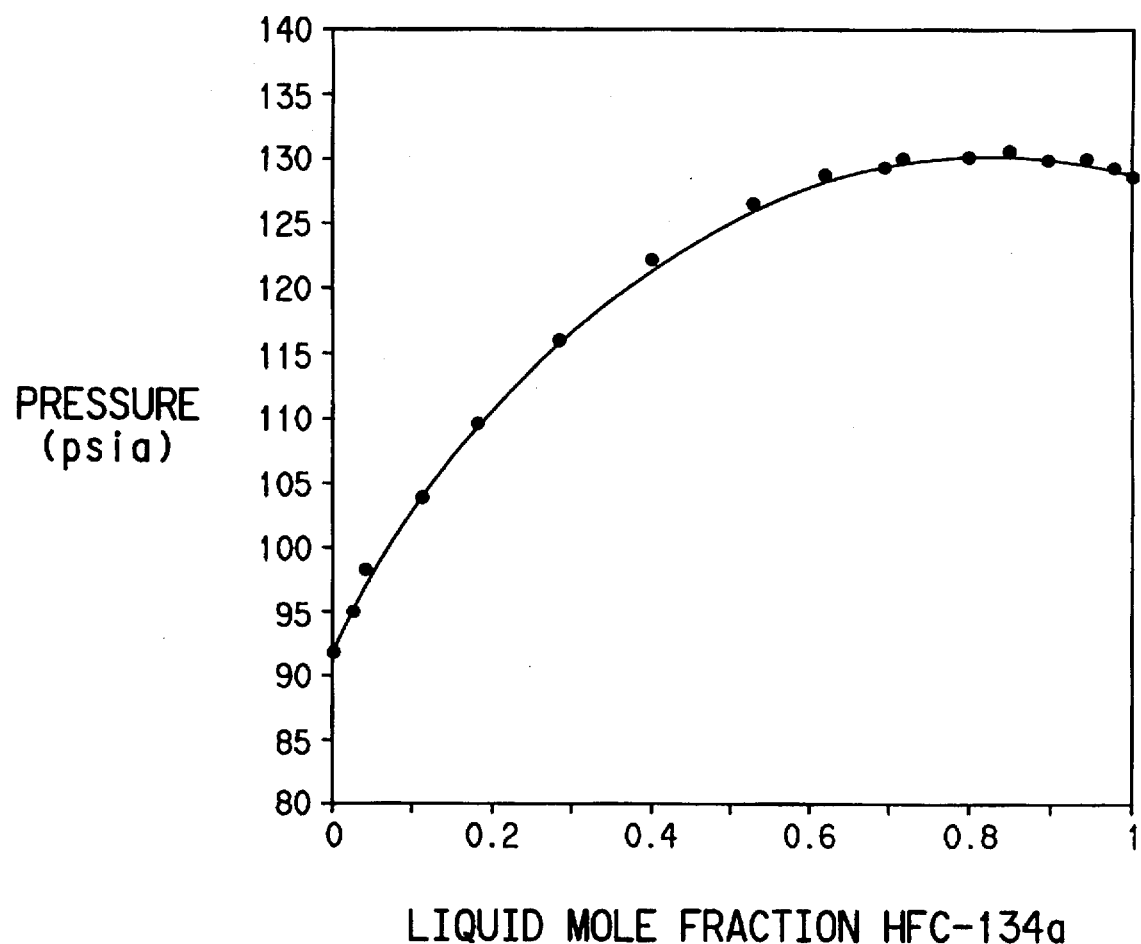
FIG. 7—FIG. 7 is a graphical representation of an azeotropic and azeotrope-like compositions consisting essentially of HFC-134a and HCFC-1122 at a temperature of about 35° C.

Referring now to FIG. 7, FIG. 7 illustrates graphically the formation of an azeotropic and azeotrope-like composition consisting essentially of HFC-134a and HCFC-1122 at 35° C., as indicated by a mixture of about 15.6 mole % HCFC-1122 and 84.4 mole % HFC-134a having the highest pressure over the range of compositions at this temperature. Based upon these findings, it has been calculated that an azeotropic or azeotrope-like composition of about 39.3 mole % HCFC-1122 and 60.7 mole % HFC-134a is formed at −50° C. and 5.0 psia and an azeotropic or azeotrope-like composition of about 16.1 mole % HCFC-1122 and about 83.9 mole % HFC-134a is formed at 40° C. and 149 psia. Accordingly, the present invention provides an azeotropic or azeotrope-like composition consisting essentially of from about 16.1 to about 39.3 mole % HCFC-1122 and from about 83.9 to about 60.7 mole % HFC-134a, said composition having a boiling point of from about −50° C. at 5.0 psia to about 40° C. at 149 psia.

While certain aspects of the invention have been described in particular detail, a person in this art would understand that other embodiments and variations are covered by the appended claims.

The following is claimed:

1. An azeotropic or azeotrope-like composition consisting essentially of from about 91 to about 99.9 mole % 1,1,2,2-tetrafluoroethane and from about 9 to 0.1 mole % 1-chloro-1,1,2,2-tetrafluoroethane, said composition having a boiling point of from about −20° C. at 14.4 psia to about 60° C. at 199 psia.

* * * * *